United States Patent [19]

Gerlinger

[11] Patent Number: 4,900,923

[45] Date of Patent: Feb. 13, 1990

[54] REFLECTANCE MEASURING APPARATUS INCLUDING A CYLINDER-SHAPED LIGHT CONDUCTING DEVICE BETWEEN THE MEASURING APERTURE AND THE SPECIMEN

[75] Inventor: Hermann Gerlinger, Aalen, Fed. Rep. of Germany

[73] Assignee: Carl-Zeiss-Stiftung, Heidenheim, Fed. Rep. of Germany

[21] Appl. No.: 358,661

[22] Filed: May 30, 1989

[30] Foreign Application Priority Data

Jun. 3, 1988 [DE] Fed. Rep. of Germany ....... 3818815

[51] Int. Cl.[4] .............................................. G01T 1/00
[52] U.S. Cl. ..................................... 250/228; 356/236
[58] Field of Search ........................... 250/228, 237 R; 356/236, 445, 446, 447, 448; 362/16, 297, 347, 350, 356, 458, 809

[56] References Cited

U.S. PATENT DOCUMENTS

| 2,358,020 | 8/1940 | Miller | 88/14 |
| 4,453,180 | 6/1984 | Juergensen | 250/228 |
| 4,523,853 | 6/1985 | Rosenbladt et al. | 356/446 |
| 4,651,262 | 3/1987 | Piironen | 262/350 |

OTHER PUBLICATIONS

J. Phys. E: Sci. Instrum., vol. 18, 1985, H. H. Schlemmer and M. Mächler "Diode Array Spectrometer: an Optimised Design" pp. 914 to 919.

Primary Examiner—David C. Nelms
Assistant Examiner—William L. Oen
Attorney, Agent, or Firm—Walter Ottesen

[57] ABSTRACT

The invention is directed to a reflectance measuring apparatus having a predetermined aperture for the receiving optic. A light-conducting device arranged between the measuring aperture and the specimen enlarges the effective measuring surface of the latter so that even specimens having a large surface structure can be measured without difficulty.

15 Claims, 2 Drawing Sheets

REFLECTANCE MEASURING APPARATUS INCLUDING A CYLINDER-SHAPED LIGHT CONDUCTING DEVICE BETWEEN THE MEASURING APERTURE AND THE SPECIMEN

FIELD OF THE INVENTION

The invention relates to a reflectance measuring apparatus having a measuring aperture for placement on the specimen to be measured. The apparatus includes a light source for illuminating the specimen and a receiving optic which detects the radiation reflected from the specimen within a predetermined aperture.

BACKGROUND OF THE INVENTION

Reflectance measuring apparatus measure the proportion of the radiation reflected from a specimen to the radiation reflected from a comparison specimen under the same conditions. For this purpose, the specimen is placed on a circularly-shaped measurement opening in many such apparatus so that the specimen is received by the measuring apparatus in a precisely defined position. Often, this measuring aperture is arranged in a so-called Ulbricht sphere by means of which the specimen is diffusibly illuminated.

With some reflectance apparatus, a so-called measuring head having all parts necessary for the measurement in the direct vicinity of the specimen is separated from the remainder of the apparatus and is connected to the latter only via a cable. In these apparatus, the measuring aperture can be brought to the specimen which is an advantage especially for large and heavy specimens. Such a reflectance measurement apparatus is described, for example, in the article entitled "Diode Array Spectrometer: an Optimised Design" by H. H. Schlemmer and M. Mächler, J. Phys. E: Sci-Instrum., Volume 18, pages 913 to 919, 1985.

The measurement opening must not exceed a specific diameter so that the measuring apparatus or the measuring head is not too large. However, since the measuring aperture must be large with respect to the surface structure of the specimen in order to obtain measurement results which are independent of which part of the specimen is by chance applied to the measuring aperture, only specimens with a sufficiently small surface structure can be reliably measured for a predetermined diameter of the measuring aperture. This is especially then a disadvantage when specimens having a large surface structure are to be measured only from time to time.

Further, an enlargement of the measurement surface on the specimen cannot be obtained by arranging the specimen in a correspondingly large spacing from the measuring aperture because not only does the illumination of the specimen become so weak that the reflected radiation is no longer adequate for measuring but also because the angular distribution of the rays incident on the measurement surface of the specimen is so changed even with small distance changes that the measurement values and therefore also the color range change considerably.

SUMMARY OF THE INVENTION

It is an object of the invention to provide a reflectance measuring apparatus which can also adequately and reproducibly measure specimens having relatively large surface structure notwithstanding a small measuring aperture.

According to a feature of the reflectance measuring apparatus of the invention, a light-conducting device which is at least approximately cylindrically shaped is placed or is placeable upon the measuring aperture. The axis of the light-conducting device is perpendicular to and disposed centrally on the surface of the measuring aperture and has a diameter and length which is selected so that the aperture of the receiving optic is at least not substantially changed and the end of the light-conducting device lying opposite the measuring aperture is provided as an enlarged measuring aperture for the specimen.

In an especially advantageous embodiment of the invention, the light-conducting device comprises a cylindrically-shaped tube which is mirrored on its inner surface. If the following conditions are present: (a) the inner diameter of the tube is, for example, greater than the diameter of the measurement surface in the measuring aperture by a factor of 1.41; and, (b) the tube is so long that at its end facing away from the measuring aperture, the aperture angle detected by the receiving optic almost touches the inner diameter; then the specimen surface detected at the end of the tube for the measurement is twice as large as when the specimen is placed directly on the measuring aperture.

According to another embodiment of the invention, the end of the tube facing the specimen can be provided closed off by a window.

In another advantageous embodiment of the invention, the light-conducting device comprises a solid, light-transmitting cylindrical part made of glass or plastic. In this case, the enlargement factor of the measurement surface is smaller by a factor of the index of refraction of the glass or plastic or the length of the light-conducting device must be increased with respect to the tube by a factor of the index of refraction. This can even be advantageous in order to reach a measurement surface on which the conventional measuring head cannot be applied because of spatial reasons.

If quantitative deviations in the color values computed from the reflectance values are permitted, then the light-conducting device can be made shorter or longer than in the embodiments discussed above. Even deviations from the cylindrical shape are possible provided that they are not too large. Furthermore, the measurement surfaces must not necessarily have circularly-shaped cross sections.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
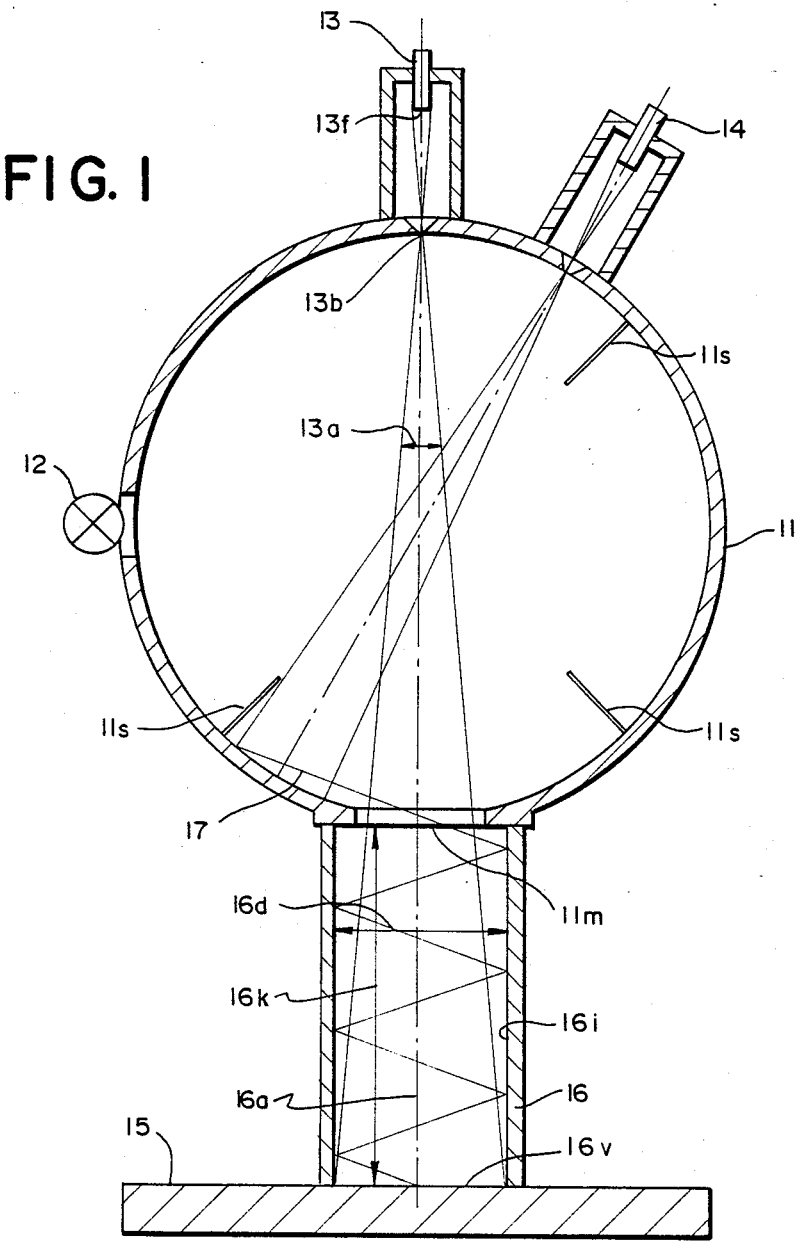
FIG. 1 is a side elevation view, in section, of a reflectance measuring apparatus having an Ulbricht sphere for diffusibly illuminating the specimen and a cylindrically-shaped tube disposed ahead of the measuring aperture; and, FIG. 2 is a side elevation view, in section, of the measuring part of a reflectance measuring apparatus having directed illumination of the specimen and a massive light conductor ahead of the measuring aperture.

In FIG. 1, reference numeral 1 identifies an Ulbricht sphere which has a measuring aperture 11m on which a specimen to be measured can be placed in the usual manner. The light source 12 diffusibly illuminates the specimen with the blinds 11s preventing a direct illumination of the specimen and of the receiving optic 13. The radiation reflected from the specimen is measured by the receiving optic 13 which detects the radiation only within a predetermined aperture 13a as a consequence of its defined receiver surface 13f and a diaphragm 13b. The receiver surface 13f can, for example, be the end face of a light conductor. A second receiving optic 14 is often provided as a reference receiving optic which detects the reflected radiation of a suitable location of the white coating of the Ulbricht sphere with the same aperture.

According to the invention, if the specimen 15 has a large surface structure, it is not placed on the measuring aperture 11m as is conventional; instead, it is placed on a cylindrically-shaped tube 16 which is mirrored on its inner surface 16i and whose axis 16a is applied perpendicularly and centrally to the surface of the measuring aperture 11m. The diameter 16d and length 16k of the cylindrically-shaped tube 16 are preferably so selected that the aperture predetermined by the receiving optic is not cropped.

As shown in FIG. 1 with the aid of a ray 17, the angular distribution of the radiation incident upon the specimen surface does not change; that is, if the dimensions of the Ulbricht sphere correspond to a standard geometry, these dimensions are maintained even with the application of the cylindrically-shaped tube. On the other hand, it is seen from FIG. 1 that an increase of the effective measurement surface on the specimen can be twice and even more if the specimen is not seated on the measuring aperture 11m as is conventional but is instead applied to the enlarged measuring aperture 16v.

If the aperture is cropped, not only is the receiver signal reduced, but also the peripheral zones of the measurement surface are overemphasized. If the inner diameter of the cylindrically-shaped tube is made too large, specific angular regions of the radiation distribution are separated out and the radiation power is weakened. Such deviations from the optimal dimensions can, however, often be tolerated to a certain extent in dependence upon the measuring task to be performed. This applies especially to color difference measurements. The same applies to deviations from the cylindrical form for the reflecting inner surface 16i with a slightly conically-shaped configuration as well as a polygonal cross section being possible.

Figure 2:
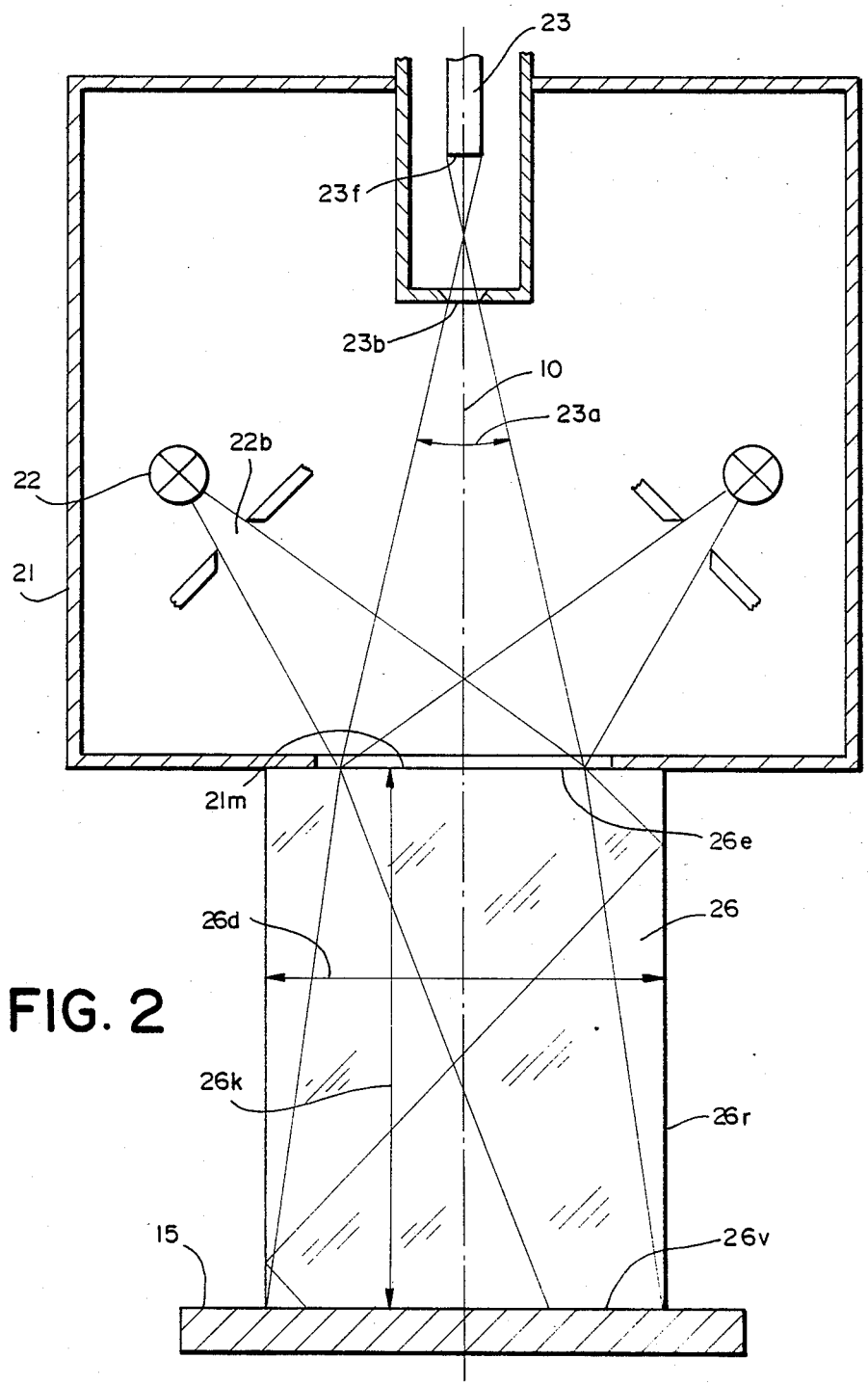

In FIG. 2, the measurement part of a reflectance apparatus having a directed illumination is shown. Reference numeral 22 identifies a ring lamp and in lieu thereof, a single or several light sources can be used which are arranged on a circle about the axis 10. The specimen is placed at the measuring aperture 21m of the housing 21 in the usual manner and is illuminated at a predetermined angle of for example 45° and most often through one or more diaphragms 22b having a predetermined aperture. The radiation reflected from the specimen is measured by means of receiving optic 23 which, as a consequence of its definable receiving surface 23f and an aperture 23b, only detects the radiation within the predetermined aperture 23a.

For the case wherein the specimen 15 has a large surface structure, a light-conducting device 26 is mounted between the specimen and the measuring aperture 21m. For the embodiment shown in FIG. 2, a light-conducting device 26 in the form of a massive, cylindrically-shaped tube made of glass or plastic is provided having an outer surface 26r which is preferably mirrored and whose end surfaces (26e, 26v) are advantageously uncoated. The diameter 26d and length 26k of the light-conducting device 26 are again preferably so selected that the aperture 23a of the receiving optic 23 is just barely not cropped and the desired enlargement of the effective measurement surface of the specimen 15 is obtained. In this embodiment also, deviations from the optimal dimensions of the light-conducting device 26 as well as deviations from the cylindrical form are possible within a predetermined limit which is dependent upon the specimen to be investigated and the measuring precision required.

The specimen 15 does not have to be directly placed on the enlarged opening 26v of the light-conducting device 26 and can instead be mounted at a defined distance therefrom.

The tube 16 of FIG. 1 can be used in the reflectance measuring apparatus shown in FIG. 2 and the massive cylinder 26 of FIG. 2 can be used in the apparatus of FIG. 1.

It is understood that the foregoing description is that of the preferred embodiments of the invention and that various changes and modifications may be made thereto without departing from the spirit and scope of the invention as defined in the appended claims.

What is claimed is:

1. A reflectance measuring apparatus for measuring a specimen, the apparatus comprising:
   a structure defining a measuring aperture having a center;
   light source means for illuminating the specimen from which light radiation is reflected;
   receiver means for detecting the radiation reflected from the specimen within a predetermined aperture;
   a light-conducting device having a first longitudinal end placed on said measuring aperture and a second longitudinal end facing the specimen;
   said light-conducting device having a configuration which is at least approximately cylinder-shaped and defining a longitudinal axis perpendicular to the area of said measuring aperture so as to extend through the center thereof; and,
   said light-conducting device having a diameter and a length selected so as to not significantly change said predetermined aperture and so as to cause said second longitudinal end to define an enlarged measuring aperture for the specimen.

2. The reflectance measuring apparatus of claim 1, said structure being a measuring head having said measuring aperture formed therein; and, a cable extending from said measuring head and adapted to be connected with another component of the apparatus.

3. The reflectance measuring apparatus of claim 1, said structure being an Ulbricht sphere having said measuring aperture formed therein.

4. The reflectance measuring apparatus of claim 1, said light-conducting device having a circularly-shaped cross section.

5. The reflectance measuring apparatus of claim 4, said light-conducting device being a tube.

6. The reflectance measuring apparatus of claim 5, said light-conducting device being a massive, light-transparent piece made of a material selected from the group consisting of glass and plastic.

7. The reflectance measuring apparatus of claim 5, said second longitudinal end of said tube being closed off by a window.

8. The reflectance measuring apparatus of claim 6, said longitudinal ends of said light-conducting device being uncoated.

9. The reflectance measuring apparatus of claim 1, said light-conducting device having a polygonal-shaped cross section.

10. The reflectance measuring apparatus of claim 9, said light-conducting device being a tube.

11. The reflectance measuring apparatus of claim 10, said light-conducting device being a massive, light-transparent piece made of a material selected from the group consisting of glass and plastic.

12. The reflectance measuring apparatus of claim 10, said second longitudinal end of said tube being closed off by a window.

13. The reflectance measuring apparatus of claim 11, said longitudinal ends of said light-conducting device being uncoated.

14. The reflectance measuring apparatus of claim 1, said light-conducting device having a wall surface disposed in surrounding relationship to said axis; and, said surface having a reflective coating formed thereon.

15. The reflectance measuring apparatus of claim 1, said light-conducting device having a wall surface disposed in surrounding relationship to said axis; and, said surface having a white coating formed thereon.

* * * * *